(12) United States Patent
Zheng et al.

(10) Patent No.: US 10,260,059 B2
(45) Date of Patent: Apr. 16, 2019

(54) NITRILASE FROM ARABIS ALPINA, ITS ENCODING GENE, VECTOR, RECOMBINANT BACTERIAL STRAIN AND USES THEREOF

(71) Applicants: Zhejiang University of Technology, Hangzhou (CN); Zhejiang Chiral Medicine Chemicals Co. Ltd., Hangzhou (CN)

(72) Inventors: Renchao Zheng, Hangzhou (CN); Yuguo Zheng, Hangzhou (CN); Qin Zhang, Zhangshi (CN); Youming Huang, Hangzhou (CN); Jianfeng Weng, Hangzhou (CN); Tianchun Liu, Hangzhou (CN); Weirong Fan, Hangzhou (CN)

(73) Assignees: Zhejiang University of Technology, Hangzhou (CN); Zhejiang Chiral Medicine Chemicals Co. Ltd., Hangzhou (CN)

( * ) Notice: Subject to any disclaimer, the term of this patent is extended or adjusted under 35 U.S.C. 154(b) by 0 days.

(21) Appl. No.: 15/687,800

(22) Filed: Aug. 28, 2017

(65) Prior Publication Data
US 2017/0355976 A1 Dec. 14, 2017

Related U.S. Application Data

(62) Division of application No. 15/246,626, filed on Aug. 25, 2016, now abandoned.

(30) Foreign Application Priority Data

Aug. 27, 2015 (CN) .......................... 2015 1 0535881

(51) Int. Cl.
C12N 9/78 (2006.01)
C12P 13/00 (2006.01)

(52) U.S. Cl.
CPC .............. *C12N 9/78* (2013.01); *C12P 13/002* (2013.01); *C12Y 305/05001* (2013.01)

(58) Field of Classification Search
None
See application file for complete search history.

(56) References Cited

U.S. PATENT DOCUMENTS 8,304,252 B2 11/2012 Burns et al.

FOREIGN PATENT DOCUMENTS

WO WO 2005/100580 10/2005

OTHER PUBLICATIONS

Uni Prot Accession No. A0A087HS97 (created on Oct. 29, 2014).*
Martinez et al., "Development of a chemoenzymatic manufacturing process for pregabilin," *Organic Process Research & Development*, 12:392-398, 2008.
Office Communication issued in U.S. Appl. No. 15/246,626, dated Jul. 17, 2017.
Silverman, "From Basic Science to Blockbuster Drug: The Discovery of Lyrica,"*Angew. Chem. Int. Ed.*, 47(19): 3500-3504, 2008.
Xie et al., "Cloning and optimization of a nitrilase for the synthesis of (3 S)-3-cyano-5-methyl hexanoic acid," *Journal of Molecular Catalysis B: Enzymatic*, 41:75-80, 2006.
YiTao et al., "Biocatalytic desymmetrization of 3-substituted glutaronitriles by nitrilases. A convenient chemoenzymatic access to optically active (S)-Pregabilin and (R)-Baclofen," *Science China Chemistry*, 57(8):1164-1171, 2014.

* cited by examiner

*Primary Examiner* — Iqbal H Chowdhury
(74) *Attorney, Agent, or Firm* — Parker Highlander PLLC

(57) ABSTRACT

The disclosure provides a nitrilase from *Arabis alpina*, which belongs to genus *Arabis*, family brassicaceae. The disclosure further provides the encoding gene, vector, recombinant bacterial strain, and the application in the manufacturing of (S)-3-cyano-5-methylhexanoic acid. The wet resting cells containing nitrilase Aa-Nit can kinetically resolve racemic IBSN at 1.2 M with a 42% conversion rate in 15 hr and >99% ee value. The disclosure provides a regio- and stereoselective method for the preparation of (S)-3-cyano-5-methylhexanoic acid. This method provides an atom economical, mild, environmental friendly industrial method to manufacture (S)-3-cyano-5-methylhexanoic acid.

7 Claims, 3 Drawing Sheets

Figure 1:
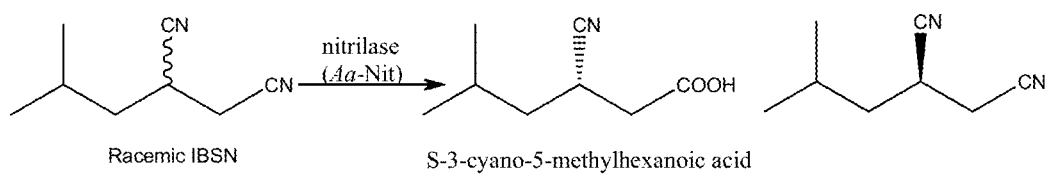

Specification includes a Sequence Listing.

NITRILASE FROM ARABIS ALPINA, ITS ENCODING GENE, VECTOR, RECOMBINANT BACTERIAL STRAIN AND USES THEREOF

This application is a divisional application of U.S. patent application Ser. No. 15/246,626, filed Aug. 25, 2016, which claims the benefit of priority to Chinese Patent Application No. 201510535881.1, filed Aug. 27, 2015, the entirety of each are incorporated herein by reference.

Pursuant to 37 C.F.R. 1.821(c), a sequence listing is submitted herewith as an ASCII compliant text file named "CCHMP0002USD2_ST25.txt", created on Aug. 24, 2017 and having a size of ~5 kilobytes. The content of the aforementioned file is hereby incorporated by reference in its entirety.

1. TECHNICAL AREA

This invention relates to a method of manufacturing (S)-3-cyano-5-methylhexanoic acid. It further relates to a nitrilase from *Arabis alpina* and the application in the manufacturing of (S)-3-cyano-5-methylhexanoic acid.

2. BACKGROUND

Pregabalin (I, PGB), chemical name (S)-3-(aminomethyl)-5-methylhexanoic acid (I), is a 3-isobutyl substituted γ-aminobutanoic acid (Angew. Chem. Int. Ed. 2008, 47: 3500-3504). PGB is very effective in treating epilepsy, diabetic neuropathy pain, and post-herpetic neuralgia pain. It requires lower dosages and less frequent administration, has fewer side effects, lasts longer, and is well tolerated. PGB has become a blockbuster in global pharmaceutical markets.

(S)-3-Cyano-5-methylhexanoic acid (II) is a key chiral intermediate that can be converted to PGB through hydrogenation. Pfizer, Inc. has developed a second-generation, enzymatic process for PGB, where 2-carboxyethyl-3-cyano-5-methylhexanoic acid ethyl ester diethyl 2-(1-cyano-3-methylbutyl)malonate was resolved through Lipolase® catalysis, decarboxylated, and hydrolyzed under basic condition to afford II (Org. Process Res. Dev. 2008, 12: 392-398). This process requires decarboxylation and two hydrolysis steps, leading to low atom economy.

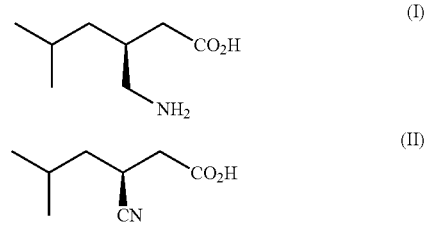

Nitrilase (EC 3.5.5.1) is an enzyme that can catalyze the hydrolysis of nitriles to ammonia and the corresponding carboxylic acid. Nitrilase has very strict regio- and stereoselectivity and shows high potential in the manufacture of highly valuable active pharmaceutical ingredients. Pfizer's Xie reported that *Arabidopsis thaliana* nitrilase At-Nit1 could regio- and stereo-selectively convert racemic 2-isobutylsuccinonitrile (ISBN) into II (J. Mol. Catal. B: Enzym. 2006, 41:75-80). This process enjoys a very high atom economy. However, nitrilase At-Nit1 has low activity and only provides II with 17.5% yield when the substrate concentration was 150 mM (WO2005100580). Another enzyme NIT-102 could only provide II at 31.3% when the substrate was treated for 24 hr at 400 mM (WO2005100580). This method is difficult to industrialize because of the long reaction time and low substrate concentration. Thus, it is very necessary to find nitrilases with industrial potential for the manufacturing of II.

SUMMARY OF THE INVENTION

The goal of the current invention is to find a novel nitrilase that can regio- and stereoselectively convert ISBN into II. The nitrilase should show higher catalytic activity and better tolerance to substrate so that II could be manufactured in industrial scale. When at 400 mM, ISBN should be converted to II at least 42%.

An embodiment of the current invention is a nitrilase (Aa-Nit) from *Arabis alpina*, which belongs to family brassicaceae. The nitrilase's amino acid sequence is shown in SEQ ID No. 1.

A further embodiment of the current invention covers any polypeptide segments or mutants obtained through knockout, insertion, replacement of one or more amino acid residues, as long as the sequence resembles 95% of SEQ ID No. 1.

Another embodiment of the current invention further covers a nitrilase's encoding gene. To realize the heterologous expression of soluble Aa-Nit in *E. coli*, the nucleotide (SEQ ID No. 2) corresponding to the amino acid sequence (SEQ ID No. 1) was synthesized through routine genetic engineering procedures.

Yet another embodiment of the current invention covers any nucleotide segments obtained through knockout, insertion, replacement of one or more nucleoside residues, as long as the sequence resembles 90% of SEQ ID No. 2.

Another embodiment of the current invention relates to a recombinant vector for the nitrilase encoding gene, and the recombinant genetically engineered bacterium obtained with the above-stated vector.

A further embodiment of the current invention relates to the method of preparing nitrilase Aa-Nit from the corresponding nitrilase gene. The nitrilase gene containing vector is introduced into the host cells to obtain the genetically engineered bacteria. The bacteria are cultured to obtain nitrilase-containing cells. The procedure is as follows: (1) Nitrilase Aa-Nit's nucleotide sequence was obtained through gene mining technique. (2) The synthesized nitrilase gene segment is inserted into pEt28b vector to afford the recombinant plasmid. (3) The recombinant plasmid is introduced into the host cell, preferably *E. coli* BL21 (DE3) to afford the corresponding engineered strain. (4) The engineered strain is inoculated into LB medium, grown to log phase, and induced with 0.1-0.2 mM IPTG at 28° C. for 12 hrs. (5) The cells are collected and the target protein size and expression is verified by SDS-PAGE electrophoresis (see FIG. 2).

Yet a further embodiment of the current invention relates to the application of nitrilase catalysis for the synthesis of II. Specifically, the engineered strain was fermented to obtain nitrilase-containing wet cells, which was used as the catalyst for the hydrolysis of racemic 2-isobutylsuccinimide in a pH 5.0-10.0 buffer (preferably in 100 mM, pH 8.0 Tris-HCl buffer) at 25-45° C. and stirred at 150 rpm (preferably at 30° C. and 150 rpm). After the hydrolysis is complete, II is isolated from the reaction mixture. The amount of catalyst used is 50 g/L of buffer based on the weight of the wet cells. The concentration of the substrate is 0.15-1.5 mol/L (preferably 0.7-1.2 mol/L).

The catalyst in the current invention is prepared as following: The nitrilase-containing engineered strain, preferably *E. coli* BL21 (DE3)/pET28b(+)-Aa-Nit, is inoculated into a liquid LB broth containing 50 μg/mL of kanamycin and grown for 12 hr at 37° C. The cultured broth was inoculated into a fresh liquid LB broth containing 50 μg/mL of kanamycin at 2% (v/v). The strain was grown at 37° C. until the cell concentration ($OD_{600}$) ca. 0.6 (0.4-0.8), and IPTG was then added to a final concentration of 0.2 mM to induce the protein expression 28° C. for 12 hr. After centrifugation at 4° C., 12000 rpm for 5 min, the wet cells are collected as catalyst.

A further embodiment of the current invention relates to the separation and purification method of II. After the reaction, the reaction mixture is centrifuged to remove *E. coli*. The supernatant is evaporated to ⅓ of the original volume. The temperature was maintained at 80° C. for 40 min to denature the proteins before the removal of the proteins through centrifugation. A preferred method of protein removal is through a further vacuum filtration. The filtrate is extracted with ethyl acetate (2× volume). The aqueous layer is acidified with 2 M HCl to pH 4.0. Extraction with ethyl acetate (2 volumes), followed by evaporation of ethyl acetate on rotavap, affords II as an oil.

The current invention provides a region- and stereoselective enzyme for the manufacturing of II through hydrolysis of IBSN. The resting cells containing nitrilase Aa-Nit can kinetically resolve IBSN at 1.2 M with the conversion rate of 42% in 15 hr and ee>99%. The current invention provides an atom economical, mild, environmental friendly industrial method to manufacture II.

ILLUSTRATIONS

FIG. 1. Nitrilase Aa-Nit catalyzed kinetic resolution of IBSN.

Figure 2:
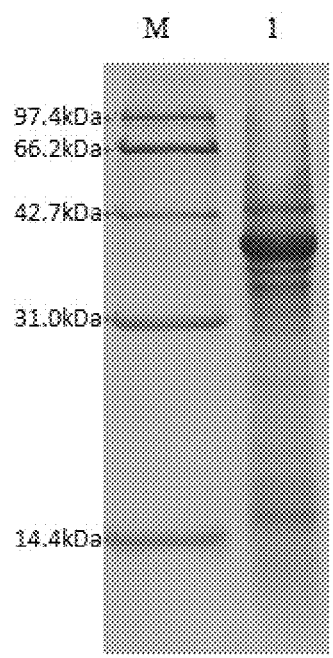

FIG. 2. SDS-PAGE analysis of Nitrilase Aa-Nit. M: Molecular weight of proteins; 1: Induced expression of the target protein.

Figure 3:
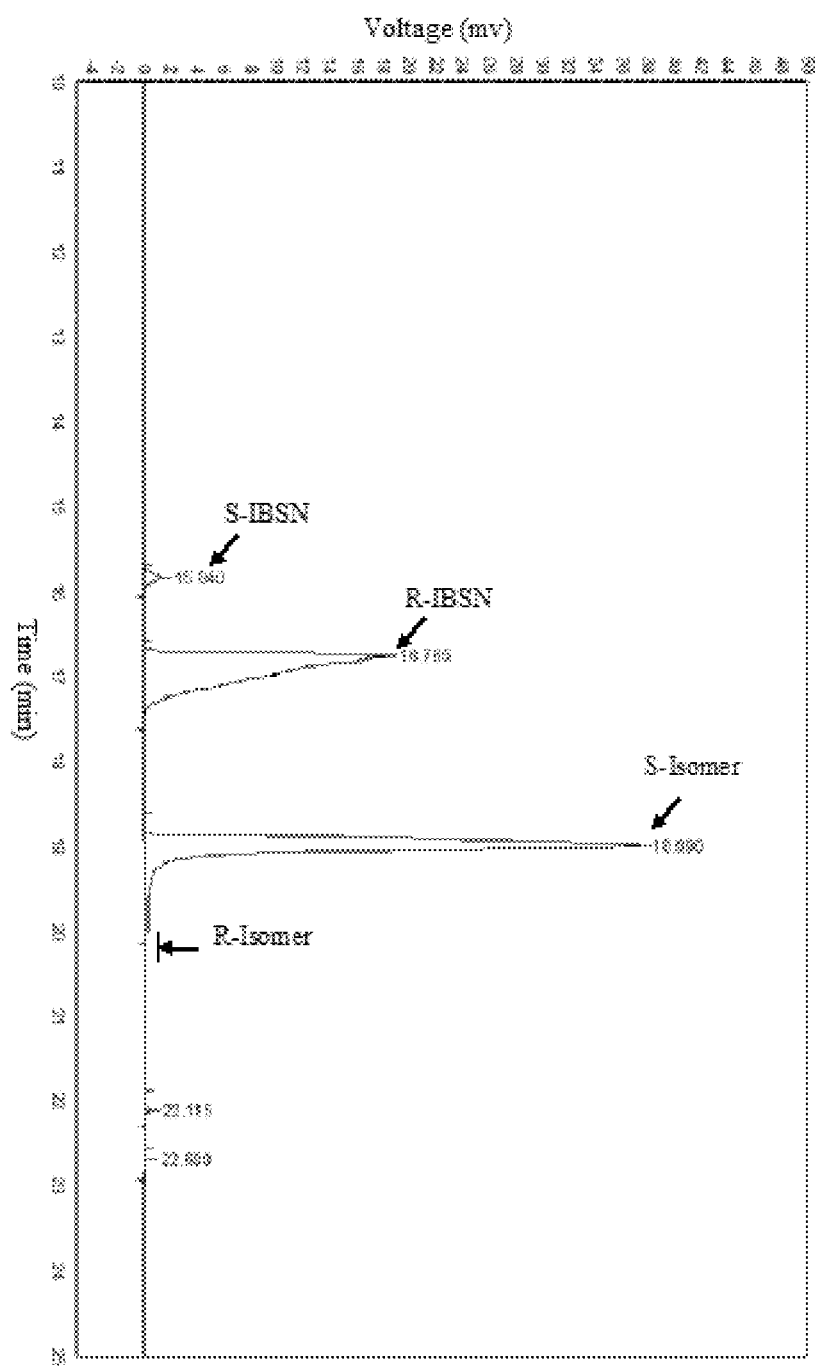

FIG. 3. Gas chromatography of nitrilase Aa-Nit catalyzed kinetic resolution of IBSN.

Figure 4:
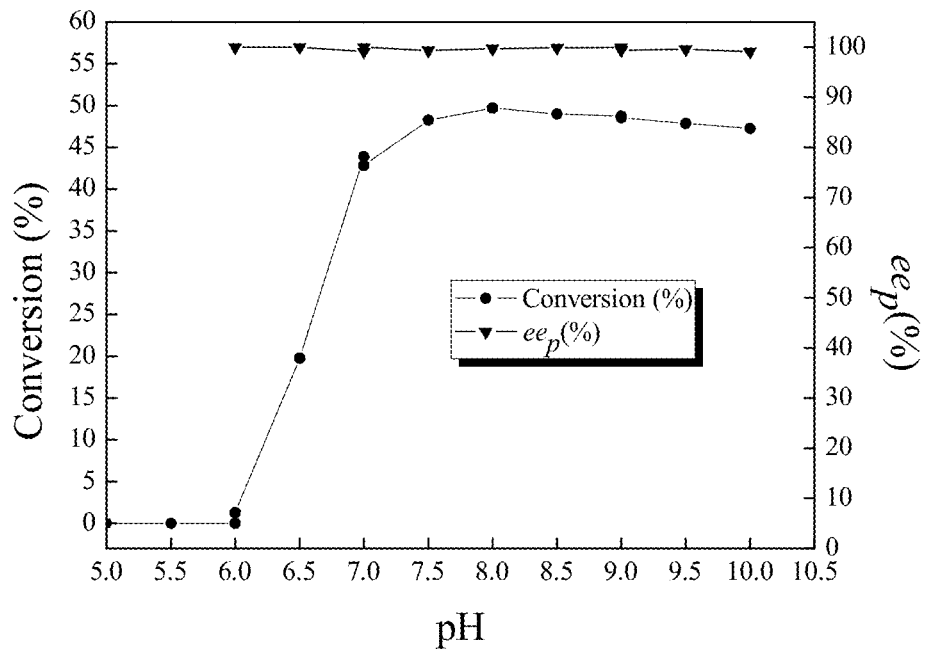

FIG. 4. Optimization of the pH of the reaction system.

Figure 5:
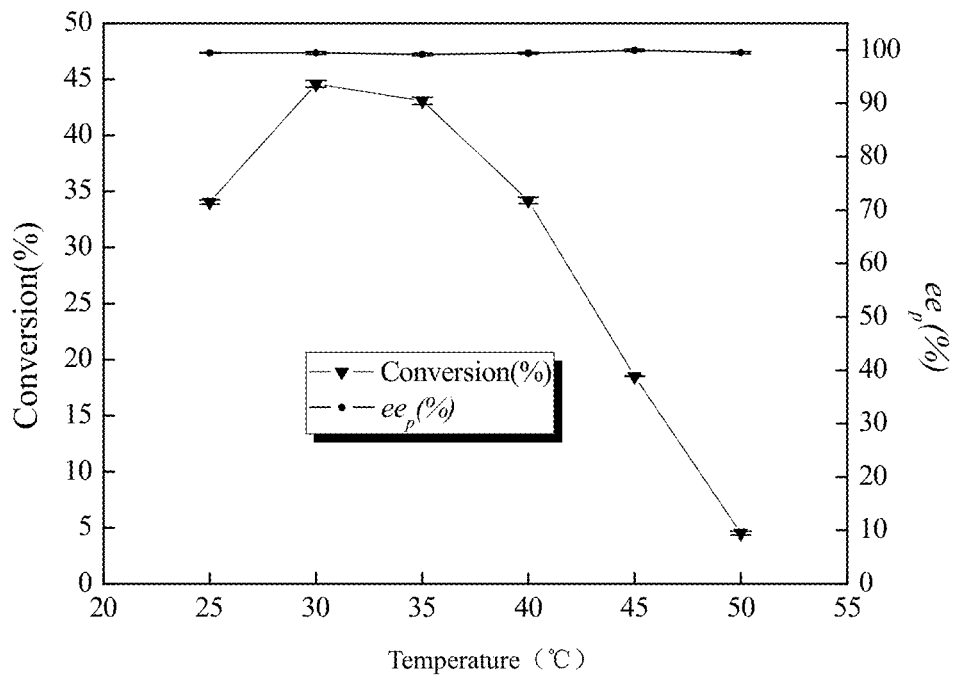

FIG. 5. Optimization of the temperature of the reaction system.

EXAMPLES

The following examples are for the illustration of the current invention and in no way represents the scope of the current invention.

The main experimental materials were purchased from the following sources:

| | |
|---|---|
| *E. coli* host strain: *E. coli* BL21 (DE3) | Invitrogen |
| Expression vector pEt-28b(+) | Novagen |
| Restriction endonucleases Xho I and Xba I | Fermentas |
| T4 DNA ligase | TaKaRa |
| Kanamycin | TaKaRa |
| IPTG | Promega |
| DNA marker and stain GoldView | TaKaRa |
| DNA gel extraction kit | Axygen |
| PCR Clean-up kit | Axygen |
| Plasmid extraction kit | Axygen |

Example 1—Preparation of Nitrilase Aa-Nit (1) Nitrilase Aa-Nit amino acid sequence and nucleic acid sequence. A nitrilase amino acid sequence (Genbank No. KFK44999.1) was obtained via screening nitrilase gene sequence from protein database PDB and NCBI. The nitrilase comes from *Arabis alpina*, a plant belong to genus *Arabis*, family Brassicaceae. Based on the amino acid sequence of nitrilase, optimized codons from *E. coli* preferred codons, and the characteristics of vector pET28b(+), restriction enzyme cutting sites Xho I and Xba I were selected. The nitrilase-coding nucleic acid (shown in SEQ ID No. 2) and the coded amino acid sequence (shown in SEQ ID No. 1) were synthesized.

(2) Construction of recombinant strain. The nucleic acid segment was treated with restriction endonucleases Xho I and Xba I and recovered. The recovered gene and commercial vector pET28b(+) (pre-treated with restriction endonucleases Xho I and Xba I) were treated with T4 DNA ligase for 16 hr at 16° C. to give Intracellular recombinant expression vector pET28b(+)-Aa-Nit, which was introduced into *E. coli* BL21 (DE3) (Invitrogen), which was then spread onto a LB agar-plate containing 50 μg/ml of kanamycin and grown overnight at 37° C. The strains grown on the plate was randomly selected and the plasmid was extracted for agarose gel electrophoresis.

(3) Induced expression of nitrilase Aa-Nit. The recombinant genetically engineered *E. coli* BL21 (DE3)/pET28b(+)-Aa-Nit was inoculated into a liquid LB broth containing 50 μg/mL of kanamycin and grown for 12 hr at 37° C. The LB broth was inoculated into a fresh liquid LB broth containing 50 μg/mL of kanamycin at 2% (v/v). The strain was grown at 37° C. until the cell concentration ($OD_{600}$) reached 0.6 and IPTG was then added to a final concentration of 0.2 mM to induce the protein expression 28° C. for 12 hr and then centrifuged at 4° C. at 12000 rpm for 5 min. The wet cells are collected (resting cells, used for hydrolysis). The wet cells were washed with physiological saline twice, mixed well, and the cell solution was analyzed with SDS-PAGE electrophoresis. The results are shown in FIG. 2.

Example 2—Catalysis with Nitrilase Aa-Nit-Containing Resting Cells

The optimal pH, temperature, pH stability and substrate tolerance were investigated.

Reaction mixture (10 mL) was composed of buffer solution (10 mL, buffer), racemic IBSN (substrate), and wet resting cells (catalyst). The substrate's concentration was 0.4 mol/L. The catalyst quantity was 20 g of wet resting cells/L. The resting cells contained 70-90% of water. The reaction was initiated in a water bath shaker at 150 rpm for 0.5 hr and terminated with 2M HCl. The conversion rate was obtained with gas chromatography to ascertian the catalytic activity of the resting cells under various conditions.

(1) Determination of optimal pH. With the catalysis system defined above, the conversion rate of racemic IBSN was determined under various pH values (pH=5, 5.5, 6, 6.5, 7, 7.5, 8, 8.5, 9, 9.5, and 10) at 30° C. with substrate concentration at 0.4 mol/L and wet resting cells at 20 g/L. The buffers for various pH were acetic acid buffer (pH=5.0-6.0), sodium phosphate buffer (pH=6.0-7.2), Tris-HCl buffer (pH=7.0-9.0), and Gly-NaOH buffer (pH=9.0-10.0).

(2) Determination of optimal reaction temperature. With the catalysis system defined above, the reaction was carried out at various temperatures (25, 30, 35, 40, and 45° C.) in Tris-HCl buffer (100 mM, pH=8.0) with the substrate concentration at 0.4 mol/L and wet resting cells of 20 g/L. The conversion rate of racemic IBSN was determined.

(3) Determination of tolerance for maximal substrate concentration. With the catalysis system defined above, the reaction was carried out at various substrate concentrations (150 mM, 300 mM, 450 mM, 600 mM, 700 mM, 1 M, 1.2 M, and 1.5 M) in 10 mL of Tris-HCl buffer (100 mM, pH=8.0) with wet resting cells of 20 g/L. The conversion rate of racemic IBSN was determined.

The results show that nitrilase Aa-Nit-containing resting cells exhibit highest catalytic activity at pH 8.0, and the optimal reaction temperature is 30° C. The maximal substrate concentration tolerated is 1.2 M.

Example 3—Application of Nitrilase Aa-Nit-Containing Resting Cells

Kinetic resolution of racemic IBSN. The reaction is shown in FIG. 1. To a Tris-HCl buffer (10 mL, 100 mM, pH 8.0) was added racemic IBSN to reach 1.2 M, and 0.5 g of wet resting cells prepared in Example 1. The mixture was shaken at 30° C. for 15 hr in a water bath shaker. A 500 µL sample was taken every 3 hr and the reaction was quenched with 200 µL of 2 M HCl. The mixture was extracted with 800 µL of ethyl acetate, shaken, and centrifuged (12000×g, 2 min). The supernatant was dried with anhydrous sodium sulfate and analyzed with gas chromatography.

(1) Determination of conversion rate and ee value with chiral gas chromatography. The amount of substrate and product present in the extract was determined with chiral gas chromatography (GC-14 C, Shimadzu, Japan). The capillary tube was BGB-174 (BGB Analytik, Switzerland). Gas chromatography conditions are below:

| | |
|---|---|
| Sample amount | 1 µL |
| Inlet and detector temperature | 220° C. |
| Column temperature | 160° C. |
| Carrier gas | Helium |
| Flow rate | 1.6 mL/min |
| Split ratio | 30:1 |

The conversion rate and ee value were calculated according to literature method reported by Rakels et al. (Enzyme Microb Technol, 1993, 15: 1051).

(2) Isolation and purification of II. After the reaction, the reaction mixture is centrifuged to remove *E. coli*. The supernatant is evaporated to ⅓ of the original volume. The temperature was maintained at 80° C. for 40 min to denature the proteins before the removal of the denatured proteins through centrifugation. The supernatant was vacuum filtered to remove more proteins. The filtrate was extracted with ethyl acetate (2× volume). The aqueous layer is acidified with 2 M HCl to pH 4.0. Extraction with ethyl acetate (2× volume), followed by evaporation of ethyl acetate on rotavap, affords II as an oil (ee>99.5%).

The results show that the resting cells containing nitrilase Aa-Nit can kinetically resolve IBSN at 1.2 M with the conversion rate at 42% in 15 hr and $ee_p$>99%. Thus, nitrilase Aa-Nit catalysis disclosed in the current invention provides a mild method to manufacture II with high conversion rate and optical purity.

It is understood that the working examples are only for illustration so that those skilled in the art would understand the current invention and be able to reduce the current invention to practice. These examples are in no way to limit the scope and extent of the current invention. Any equivalent modifications or changes based on the current invention should be covered by the current invention.

REFERENCES CITED

Enzyme Microb Technol, 1993, 15: 1051
Org. Process Res. Dev. 2008, 12: 392-398
Angew. Chem. Int. Ed. 2008, 47: 3500-3504
J. Mol. Catal. B: Enzym. 2006, 41: 75-80
WO2005100580

---

What we claim:

1. A method of producing (S)-3-cyano-5-methyl hexanoic acid comprising performing hydrolysis of racemic 2-isobutylsuccinimide using an *Arabis alpina* nitrilase comprising the amino acid sequence of SEQ ID NO: 1.

2. The method of claim 1, wherein the nitrilase gene comprising, recombinant bacterial strain is fermented and grown to provide wet cells comprising the nitrilase.

3. The method of claim 2, where the amount of nitrilase gene comprising, recombinant bacterial strain used for hydrolysis is 50 g/L based on the weight of the wet cells.

4. The method of claim 2, wherein (a) the nitrilase gene comprising, recombinant bacterial strain is inoculated into a liquid LB broth containing 50 pg/mL of kanamycin and is grown for 12 hr at 37° C.; (b) the LB broth of step (a) is inoculated into fresh liquid LB broth containing 50 pg/mL of kanamycin at 2% (v/v); (c) the nitrilase gene comprising, recombinant bacterial strain is grown to cell concentration (OD600) 0.4-0.8 at 37° C.; IPTG is added to the LB broth of step (b) until the concentration reaches 0.2 mM, (d) the gene comprising, recombinant bacterial strain is induced to grow at 28° C. for 12 hr; the LB broth of step (c) is centrifuged at 4° C. at 12000 rpm for 5 min; and (e) the wet cells are collected.

5. The method of claim 2, wherein hydrolysis of racemic 2-isobutylsuccinimide takes place at a pH 5.0-10.0 in a buffer, at 25-45° C. while stirring at 150 rpm.

6. The method of claim 2, wherein (S)-3-cyano-5-methylhexanoic acid is isolated and purified from the reaction mixture following hydrolysis.

7. The method of claim 3, wherein the concentration of racemic 2-isobutylsuccinimide is 0.15-1.5 mol/L.

* * * * *

SEQUENCE LISTING

```
<160> NUMBER OF SEQ ID NOS: 2

<210> SEQ ID NO 1
<211> LENGTH: 346
<212> TYPE: PRT
<213> ORGANISM: Arabis alpina

<400> SEQUENCE: 1

Met Ser Gly Lys Glu Glu Met Ser Ser Val Lys Asn Thr Thr Pro Ala
1               5                   10                  15

Asn Gly Val Ala Pro Ser Ser Ile Val Arg Ala Ser Ile Val Gln Ala
            20                  25                  30

Ser Thr Val Tyr Asn Asn Thr Pro Ala Thr Leu Glu Lys Ala Glu Lys
        35                  40                  45

Leu Ile Ala Glu Ala Ala Ser Asn Gly Ser Lys Leu Val Val Phe Pro
    50                  55                  60

Glu Ala Phe Ile Gly Gly Tyr Pro Arg Gly Phe Arg Phe Gly Ile Gly
65                  70                  75                  80

Val Gly Val His Asn Glu Asp Gly Arg Asp Glu Phe Arg Asn Tyr His
                85                  90                  95

Ala Ser Ala Ile Arg Val Pro Gly Pro Glu Val Glu Lys Leu Ala Glu
```

```
            100                 105                 110
Val Ala Gly Lys Asn Asn Val Tyr Leu Val Met Gly Ala Ile Glu Lys
            115                 120                 125
Asp Gly Tyr Thr Leu Tyr Cys Thr Ala Leu Phe Phe Ser Ser Gln Gly
            130                 135                 140
Leu Phe Leu Gly Lys His Arg Lys Leu Met Pro Thr Ser Leu Glu Arg
145                 150                 155                 160
Cys Ile Trp Gly Tyr Gly Asp Gly Ser Thr Ile Pro Val Tyr Asp Thr
                165                 170                 175
Pro His Gly Lys Leu Gly Ala Ala Ile Cys Trp Glu Asn Arg Met Pro
                    180                 185                 190
Leu Tyr Arg Thr Ala Leu Tyr Ala Lys Gly Val Glu Ile Tyr Cys Ala
                        195                 200                 205
Pro Thr Ala Asp Gly Ser Lys Glu Trp Gln Ser Ser Met Leu His Ile
                            210                 215                 220
Ala Leu Glu Gly Gly Cys Phe Val Leu Ser Ala Cys Gln Phe Cys Arg
225                 230                 235                 240
Arg Lys Asp Phe Pro Asp His Pro Asp Tyr Leu Phe Thr Asp Trp Asp
                245                 250                 255
Asp Asn Gln Glu Asp His Ala Ile Val Ser Gln Gly Gly Ser Val Ile
                    260                 265                 270
Ile Ser Pro Leu Gly Gln Val Leu Ala Gly Pro Asn Phe Glu Ser Glu
                        275                 280                 285
Gly Leu Val Thr Ala Asp Leu Asp Leu Gly Asp Val Ala Arg Ala Lys
            290                 295                 300
Leu Tyr Phe Asp Val Val Gly His Tyr Ser Lys Pro Glu Val Phe Asn
305                 310                 315                 320
Leu Thr Val Asn Glu Asp Arg Lys Lys Pro Val Thr Phe Val Ser Lys
                325                 330                 335
Val Glu Lys Ala Glu Asp Glu Pro Lys Lys
            340                 345

<210> SEQ ID NO 2
<211> LENGTH: 1038
<212> TYPE: DNA
<213> ORGANISM: Arabis alpina

<400> SEQUENCE: 2
atgtctggta aagaagaaat gtcttctgtt aaaaacacca ccccggctaa cggtgttgct     60
ccgtcttcta tcgttcgtgc ttctatcgtt caggcttcta ccgtttacaa caacaccccg    120 gctacccctgg aaaaagctga aaaactgatc gctgaagctg cttctaacgg ttcgaagctg    180
gttgtattcc cggaagcgtt catcggcggt tacccacgtg gctttaggtt cggtataggt    240
gttggtgttc acaacgaaga cggtcgtgac gaattccgta actaccacgc ttctgctatc    300
cgtgttccgg gtccggaagt tgaaaaactg gctgaagttg ctggtaaaaa caacgtttac    360
ctggttatgg gtgctatcga aaaagacggt tacaccctgt actgcaccgc tctgttcttc    420
tcttctcagg gtctgttcct gggtaaacac cgtaaactga tgccgacctc tctggaacgt    480
tgcatctggg gttacggtga cggttcgact atcccggtta cgacacacc gcacggtaaa    540 ctgggtgctg ctatctgctg ggaaaaccgt atgccgctgt accgtaccgc tctgtacgct    600
aaaggtgttg aaatctactg cgctccgacc gctgacggtt ctaaagaatg cagtcttct    660 atgctgcaca tcgctctgga aggtggttgc ttcgttctgt ctgcttgcca gttctgccgt    720
```

```
cgtaaagact tcccggacca cccggactac ctgttcaccg actgggacga caaccaggaa        780
gaccacgcta tcgtttctca gggtggttct gttatcatct ctccgctggg tcaggttctg        840
gctggtccga acttcgaatc tgaaggtctg gttaccgctg acctggacct gggtgacgtt        900
gctcgtgcta aactgtactt cgacgttgtt ggtcactact ctaaaccgga agttttcaac        960
ctgaccgtta acgaagaccg taaaaaaccg gttaccttcg tttctaaagt tgaaaaagct       1020
gaagacgaac cgaaaaaa                                                     1038
```